United States Patent [19]

Fearnot

[11] Patent Number: 5,100,423
[45] Date of Patent: Mar. 31, 1992

[54] ABLATION CATHETER

[75] Inventor: Neal E. Fearnot, West Lafayette, Ind.

[73] Assignee: Medical Engineering & Development Institute, Inc., West Lafayette, Ind.

[21] Appl. No.: 570,384

[22] Filed: Aug. 21, 1990

[51] Int. Cl.$^5$ .................. A61B 17/22; A61B 17/39
[52] U.S. Cl. .................. 606/159; 606/45; 606/48; 606/169; 604/22
[58] Field of Search .......... 606/41, 42, 45, 47, 606/48, 50, 127, 126, 159, 169, 170, 198, 200, ; 604/22

[56] References Cited

U.S. PATENT DOCUMENTS

| | | | |
|---|---|---|---|
| 2,816,552 | 12/1957 | Hoffman | 606/170 X |
| 3,996,938 | 12/1976 | Clark | 606/198 X |
| 4,014,343 | 3/1977 | Esty | 128/303.14 |
| 4,032,738 | 6/1977 | Esty et al. | 200/157 |
| 4,273,128 | 6/1981 | Lary | 606/159 |
| 4,650,466 | 3/1987 | Luther | 606/198 X |
| 4,709,698 | 12/1987 | Johnston et al. | 128/303.12 |
| 4,790,812 | 12/1988 | Hawkins, Jr. et al. | 606/159 X |
| 4,890,611 | 1/1990 | Monfort et al. | 606/159 |
| 4,921,484 | 5/1990 | Hillstead | 606/159 X |
| 4,936,281 | 6/1990 | Stasz | 606/48 |
| 4,976,711 | 12/1990 | Parins et al. | 606/48 |

Primary Examiner—Lee S. Cohen
Attorney, Agent, or Firm—Richard J. Godlewski

[57] ABSTRACT

An ablation catheter is provided with an elongated member or shaft and a plurality of helically-shaped cutting wires attached to the shaft to form a cutting basket. Each of the cutting wires has a section formed as a circumferentially subscribing arc and together the wires present a circumferential cutting area of an essentially cylindrical configuration. Obstructing matter on the inner surface of a vessel cavity, such as a blood vessel or the like, is separated from the surface as the catheter is moved through the vessel. The catheter may be inserted in a vessel in a standard fashion using a wire guide which extends through a longitudinal passageway in the shaft and a hub interconnecting the basket wire. The shaft and basket together may be contained in an outer sheath to facilitate insertion. The outer sheath with the basket in a collapsed state in the outer sheath may be readily moved past an obstruction, and the sheath withdrawn to allow the basket to expand and come in contact with the interior surface of the vessel cavity. The proximal ends of the cutting wires extend from the shaft through a vibratory transducer, and the distal ends are connected together by a hub. Electrical current is applied to electrical terminals connected to the cutting wires at the proximal end of the shaft to heat the wires to facilitate separating obstructing matter from a vessel surface. Furthermore, the vibration transducer vibrates the cutting wires to further aid in separating plaque and obstruction from soft tissue such as the intima layer of the wall of a blood vessel.

25 Claims, 4 Drawing Sheets

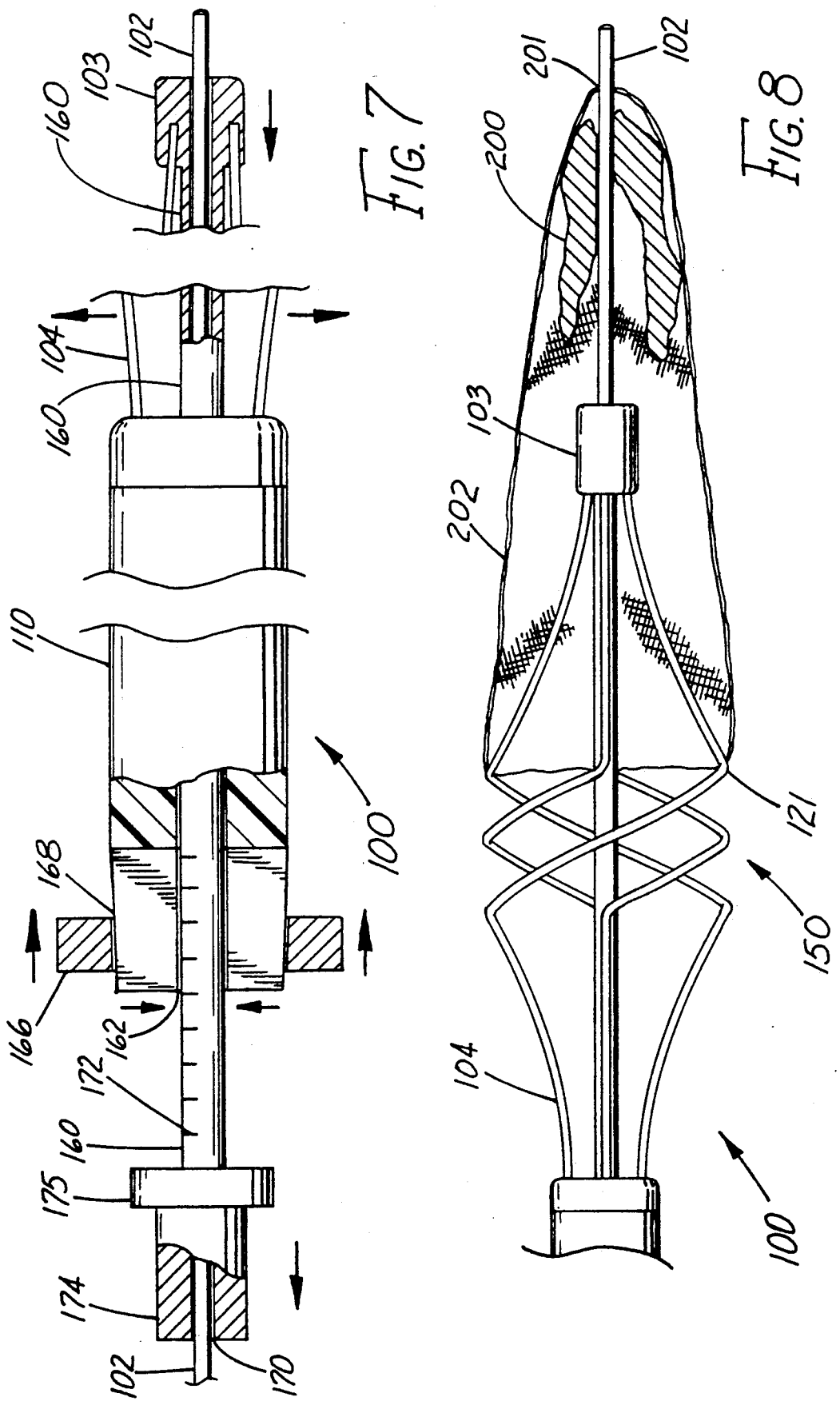

ABLATION CATHETER

TECHNICAL FIELD

The invention relates to a method and medical apparatus for removing tissue and obstructions in the vessels, ducts, and cavities of the human body and, in particular, to a percutaneously inserted catheter to remove layers of tissue and constricting obstructions from such vessels, ducts, and cavities.

BACKGROUND OF THE INVENTION

It is commonly known that constrictions in blood vessels can lead to heart problems. As a result, patients are generally urged to exercise and maintain a proper diet in order to avoid debilitating obstruction of the blood vessels. Opening of constricted blood vessels has been a problem to the medical profession for many years. It has been proposed that catheters provided with rigid dilator devices or balloon dilators or heated balloon dilators be inserted in blood vessels to enlarge the fluid passageway in constricted blood vessels.

An example of one prior art device is found in U.S. Pat. No. 4,709,698 to J. H. Johnston et al. (dated Dec. 1, 1987) which discloses a heatable dilation catheter. This prior art catheter is provided with an inflatable balloon with heating elements attached to it. The catheter is inserted in a blood vessel, and the balloon is expanded to dilate the vessel in the area of the obstruction. The heating elements are used to treat the vessel wall tissue to give it a hardened, leathery consistency to cause the vessel wall to retain the expanded dilated configuration. The treatment of the vessel wall is accomplished by applying electrical current directly to the tissue. Heating element electrodes of opposite polarity are placed in contact with the tissue in the area to be treated causing the tissue to be heated by current flowing between the electrodes. This and other prior art approaches to the problem of constricted vessels have the serious disadvantage that the dilating action forces the offending matter aside without removing the obstructing matter from the vessel. The result is that constrictions recur in the same areas and require repeated treatments to provide an adequate passage.

SUMMARY OF THE INVENTION

These and other problems of the prior art are overcome in accordance with the present invention by separating the matter causing the obstruction from the wall of the blood vessel or the like by means of an ablation catheter provided with a cutting device having one or more cutting edges. The catheter, which comprises an elongated member such as a shaft with the cutting device extending from its distal end, is inserted in an obstructed vessel by means of a percutaneous insertion procedure. The cutting edges contact the vessel wall, and movement of the catheter in the vessel in the area of an offending obstruction causes the matter forming the obstruction to be separated from the interior wall of the vessel. In one particular embodiment, the cutting device comprises a plurality of preformed, helically-shaped cutting wires, each comprising a curved section formed as a circumferentially subscribing arc. Together, the wires present a circumferential cutting area forming an essentially cylindrical configuration for engaging the circumference of the inner vessel wall. Advantageously, obstructing matter disposed around the inner circumference of a vessel wall is separated from the vessel wall by means of the cutting device to allow unobstructed fluid flow in the vessel.

In one embodiment of the invention, the catheter includes an outer sheath. The cutting wires are flexible and in one configuration are slidably contained within the outer sheath in a collapsed state. Advantageously, the catheter may be inserted in a blood vessel or the like and moved past an obstruction while the cutting wires are maintained in the collapsed state within the outer sheath. The outer sheath may then be withdrawn, allowing the cutting wires to expand and to be brought in contact with the inner wall of the vessel. As the shaft to which the wires are attached is withdrawn, the cutting wires separate the obstructing matter from the vessel wall.

In a particular embodiment of the invention, the catheter is provided with an adjustment rod for controlling the degree of expansion, and hence the size of the circumferential cutting area of the cutting device. The adjustment rod is slidably contained in a longitudinal passageway of the shaft and engages the distal end of the cutting wires. The circumferential cutting area formed by the cutting wires is adjusted by extending and withdrawing the adjustment rod relative to the shaft. Advantageously, the cutting device may be controlled by selective operation of the rod at its proximal end to make cuts of varying depth in a vessel wall.

In one embodiment of the invention, the cutting device is provided with a particulate collecting net to capture matter separated from the vessel wall. Advantageously, in accordance with this invention the obstructing matter, such as plaque deposits in a blood vessel, is separated from the vessel wall by the cutting device on the catheter, and the particulate is collected in the net and removed from the patient's system as the catheter is withdrawn.

In accordance with one aspect of the invention, a vibrating force is applied to the cutting device by means of an ultrasound transducer disposed on the movable catheter shaft. Advantageously, the ultrasonic vibrations aid in separating hard plaque from softer tissue such as the intima layer of the wall of a blood vessel.

In accordance with another aspect of the invention, electrical current is passed through individual cutting wires of the cutting device to apply heat to the wires. Advantageously, the heat applied to the vessel walls via the wires tends to melt constricting matter such as cholesterol or plaque further aiding in the removal of obstructing matter from a vessel wall. The melted materials harmlessly enter the patient's venous system. The heating and the vibrating cutting action are advantageously incorporated either singly or in combination in a single catheter to allow for the efficient separation of obstructing matter which may include material such as collagen which is resistant to heat.

BRIEF DESCRIPTION OF THE DRAWING

FIG. 7 is a fragmentary cross-sectional view showing the various cooperating parts of a catheter in accordance with the invention;

FIG. 8 is a fragmentary cross-sectional view of an

DETAILED DESCRIPTION

Figure 1:
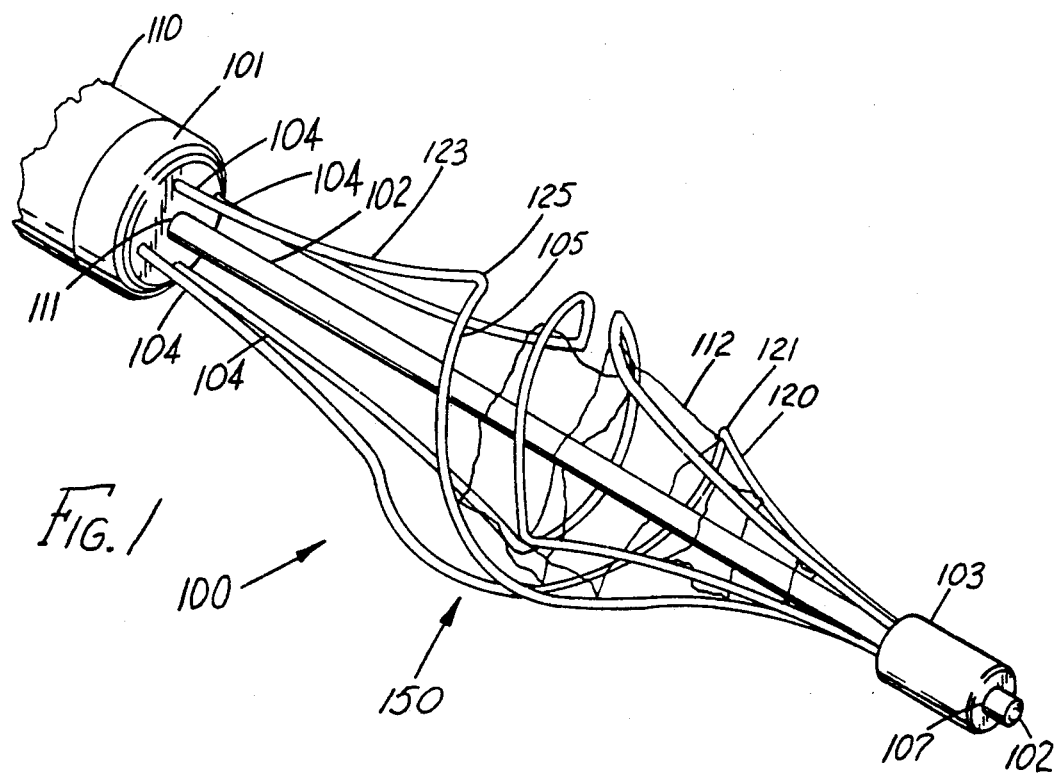
FIG. 1 is a fragmentary perspective view of an ablation catheter, incorporating the principles of the invention.

FIG. 1 is a perspective view of an ablation catheter illustrating the principles of the invention. The catheter 100 comprises an elongated member or shaft 110 for insertion in a vessel, duct, or cavity of the human body. The shaft is provided, at its distal end, with four helically-shaped, flexible wires 104 forming a wire basket 150. Each of the wires 104 comprises an arcuate curved section 105 formed as a circumferentially subscribing arc and a proximal end extending from the distal end of elongated member shaft 110 and ultrasound transducer 101. The wires 104 further each have a distal end terminating in hub 103. The catheter may be percutaneously inserted in a vessel, such as a blood vessel, in a standard fashion by the well-known method of first inserting a wire guide in the vessel and subsequently inserting the catheter over the wire guide. FIG. 1 shows wire guide 102 extending through central passageway 107 that extends longitudinally through hub 103 and through longitudinal passageway 111 in shaft 110. After the wire guide has been inserted in a blood vessel, the catheter may be inserted over the wire guide and into the vessel. The flexible cutting wires 104 will generally be in contact with the interior wall, lining, or surface of the vessel as the catheter is moved in the vessel. When an obstruction in the vessel is reached, the end portion of the catheter with the wires 104 is preferably moved past the obstruction and then withdrawn. In the process of withdrawal, the arcuate curved sections 105 of the wires 104 contact the wall of the vessel to separate obstructing matter from the wall of the blood vessel. The wire basket 150 is provided with a particulate collecting net formed by a plurality of threads 112 such as suture material attached with, for example, a medical grade adhesive to the wires 104 at a number of spaced apart positions. The net formed by the several threads 112 captures the matter separated from the vessel wall by the wire basket as the catheter is moved through a blood vessel or the like.

Each of the wires 104 is provided with a gradually outwardly extending section 120 near hub 103 to facilitate entry of the catheter in a blood vessel and past a constricting obstruction. The curved section 105 of each of the wires terminates in a nearly right angle corner 121 where the curved section 105 joins the outwardly extending section 120. Each of the wires 104 is similarly provided with a gradually expanding section 123 at its proximal end and the curved sections 105 similarly terminate on sections 123 in a nearly right angle corner 125. The nearly right angle corners 121 and 125 are further illustrated in the side elevation of FIG. 2. The corners increase the lateral orientation of each circumferentially subscribing arc with respect to the elongated member shaft as well as the longitudinal axis of the body cavity or vessel. The flexible wires 104 may, for example, be stainless steel wires having a diameter in the range of 0.006 to 0.010″. Alternatively, a superelastic metallic alloy wire may be used having a superelastic state above its transformation temperature, such as Nitinol, a well-known nickel-titanium alloy. Tantalum may also be used or included for greater radiopacity.

Figure 2:
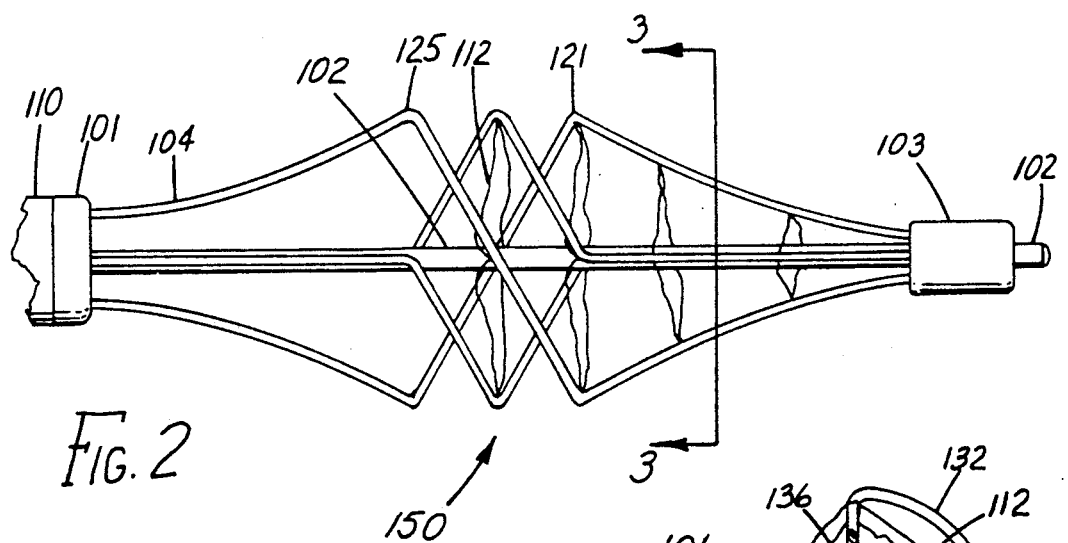
FIG. 2 is a fragmentary side elevation of the device of FIG. 1.
Figure 3:
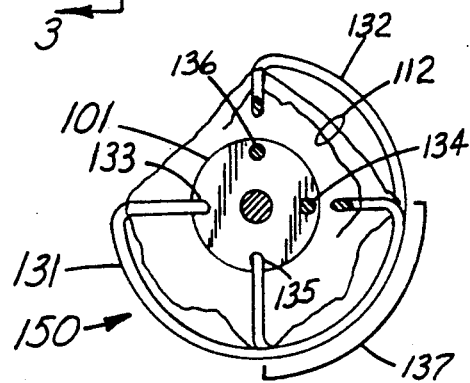
FIG. 3 is a partial fragmentary cross section of the device of FIG. 1 along line 3—3 of FIG. 2.

The curved sections 105 of the four wires are formed in an overlapping arrangement which is demonstrated in FIG. 3, which is a cross section along line 3—3 of FIG. 2. For the sake of clarity, only two of the wires, labeled 131 and 132 in FIG. 3, are shown. Wire 131 originates at point 133 on the end cap transducer 101, and wire 132 originates at point 135 on end cap transducer 101. Wire 131 overlaps wire 132 in a quarter of the circumference of the wire basket 150, as shown at 137. In a similar manner, wire 132 overlaps a portion of an adjacent wire (not shown in FIG. 3) originating from point 134. The wire originating from point 134 would similarly overlap a wire originating from point 136 on end cap transducer 101. In this manner, the wire basket presents a circumferentially extending cutting surface to the interior wall of a blood vessel or the like.

Figure 4:
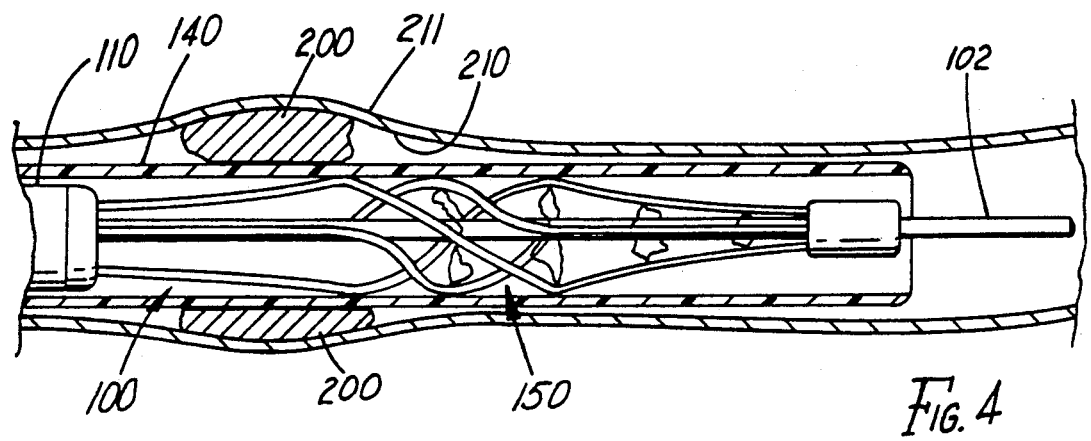
FIGS. 4 through 6 present a cross-sectional view of a blood vessel and the device of FIG. 1 disposed within the blood vessel in various configurations.
Figure 5:
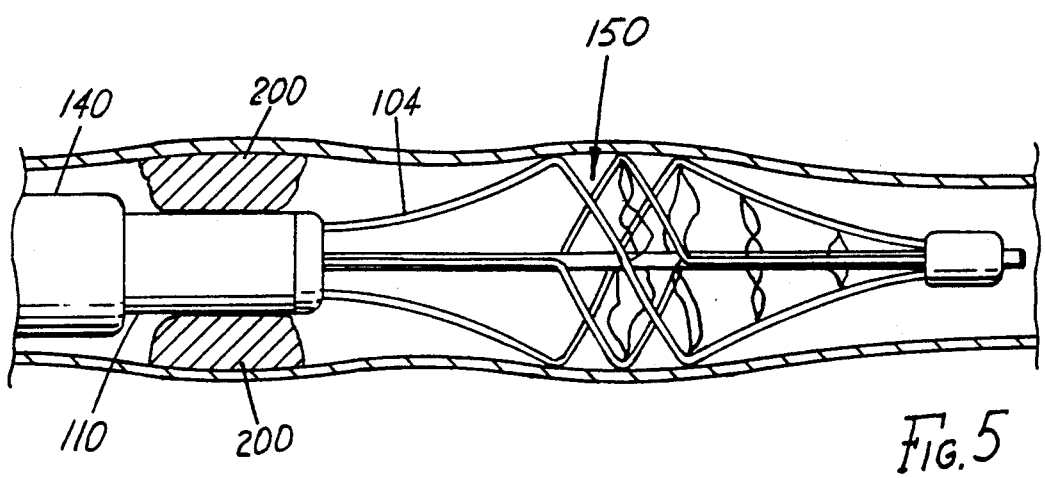
Figure 6:
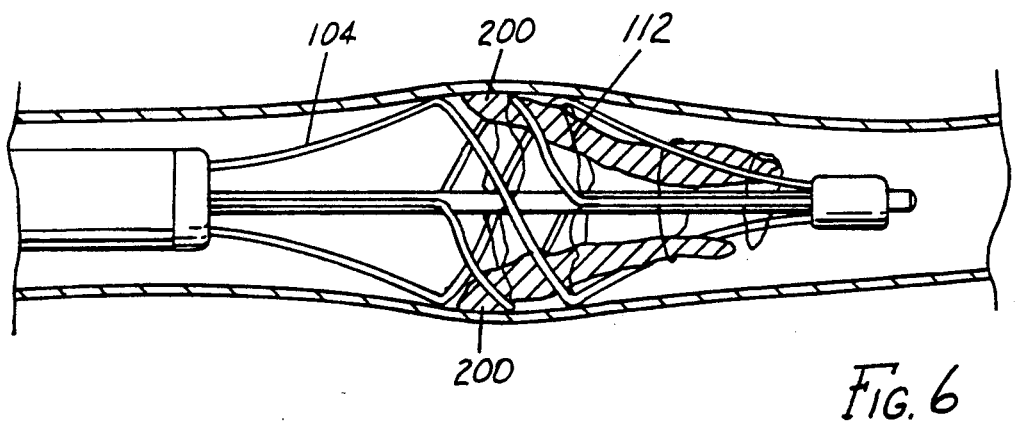

To facilitate insertion of the catheter 100 in an obstructed vessel, the catheter may be provided with an outer sheath or guiding catheter for containing the shaft 110 and particularly for maintaining wire basket 150 in a compressed configuration. FIG. 4 depicts the shaft 110 and wire basket 150 contained within sheath 140 and disposed within a vessel 211 having an inner wall 210 and constricting obstructions 200. In preparation for insertion of the catheter, a wire guide 102 is inserted in the blood vessel or the like using a well-known radiological procedure. The shaft 110 and wire basket 150 are inserted over the wire guide while positioned within the outer sheath 140. Preferably, the sheath is extended beyond a constricted area such as that formed by obstructions 200 on the inner wall 210 of vessel 211. The sheath 140 is withdrawn to allow wire basket 150 to assume an expanded configuration as depicted in FIG. 5. The shaft 110 may then be withdrawn bringing the cutting wires 104 in contact with the obstructions 200 and causing the matter forming the obstructions to be separated from the vessel wall, as depicted in FIG. 6. As the matter forming the obstructions is cut away from the wall, it is collected in the particulate collecting net formed by the several threads 112 extending between the cutting wires 104. In this manner, the obstructing deposit is separated from the wall of the vessel and the particulate is removed from the vessel as the catheter is withdrawn. The threads which form the net may be suture or other suitably strong but flexible filament which will not interfere with the collapsing of the wire basket 150 when it is drawn into the sheath 140. It is also contemplated that the expanded basket may be pushed forward to separate the obstructions from the vessel wall.

FIG. 7 discloses a further enhancement to the catheter 100 which provides control over the degree of lateral expansion of the wire basket 150. An adjustment rod 160 extends longitudinally through shaft 110 as shown in the fragmentary side view of FIG. 7. The adjustment rod 160 has a distal end attached to hub 103 and is provided at its proximal end with a cylindrically-shaped handle 174, including a shoulder 175. The rod 160 slidably engages a longitudinally-extending passageway 162 in shaft 110. Movement of the rod 160 in a direction such that the handle 174 is moved away from the shaft 110, causes the hub 103 to be moved toward shaft 110 and causes the cutting wires 104 to extend laterally, thereby increasing the cross-sectional area of the basket 150. Conversely, as the rod 160 is moved in a direction wherein the handle 174 is moved toward the shaft 110, the hub 103 is moved away from the shaft 110 causing the cutting wires 104 to be expanded longitudinally, thereby reducing the cross-sectional area of the basket 150. It will be readily apparent from the perspective view of FIG. 1 that the circumference of the basket 150 will be expanded as hub 103 is moved in the direction of the shaft 110 and that its circumference will be reduced as the hub 103 is moved away from the shaft 110. The adjustment rod 160 is provided with gradation markings 172 which correspond to degrees of expansion of the basket 150 and may be readily used by a physician to expand the basket by a precise amount while the basket is disposed internal to a vessel. A sliding lock ring 166 engages the tapered proximal end portion 168 of shaft 110. As the lock ring 166 is moved in the direction of the main portion of the shaft 110, the end portion 168 of shaft 110 will be compressed to maintain the adjustment rod 160 at a desired position. A wire guide 102 is shown disposed in a longitudinally extending passageway 170 of the adjustment rod 160.

FIG. 8 is an alternative embodiment of a net for collecting particulate 200 resulting from the cutting action of the wire basket 150. The net 202 may be formed of a gauze material or nylon netting and is attached to the cutting wires 104 in the proximity of the near 90-degree corners 121. The net 202 extends longitudinally beyond the hub 103 at the distal end of the catheter 100. The net 202 is provided with a central opening 201 at its distal end to allow for passage of the wire guide 102.

Figure 9:
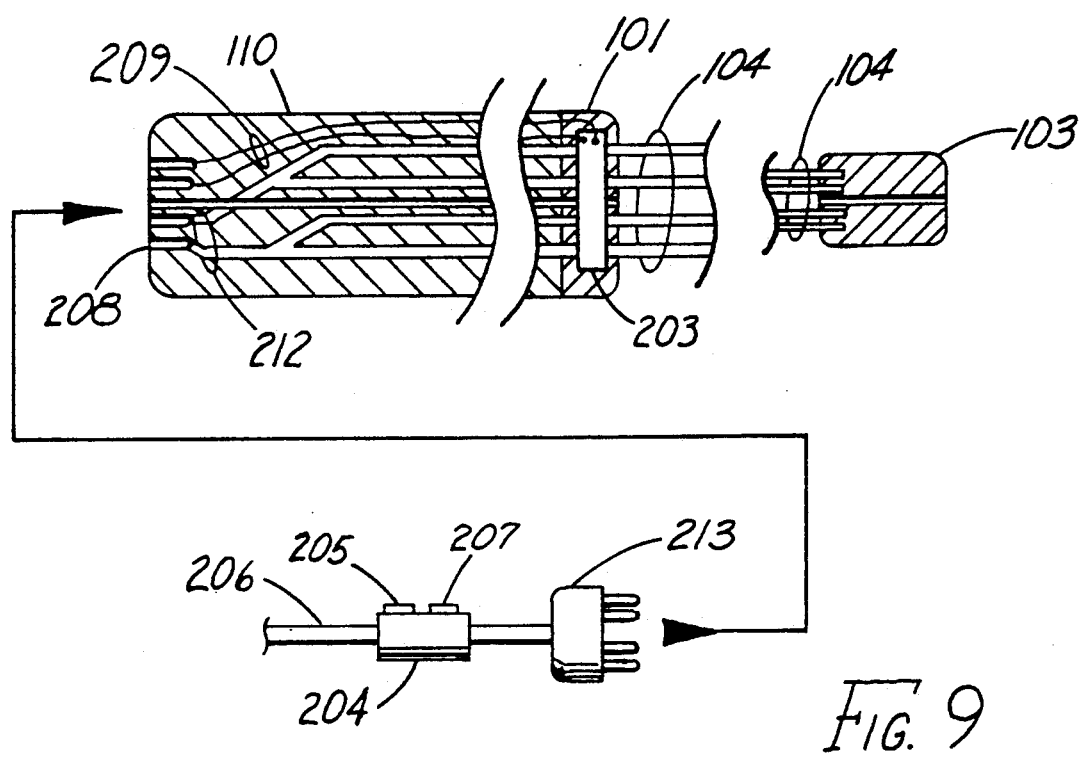
FIG. 9 is a schematic representation showing various electrical connections.

To enhance the cutting action of the cutting wires 104 and to melt obstructing material such as cholesterol or plaque or ablate soft tissue such as the mucosa of a gallbladder, the cutting wires may be heated by means of the application of electrical current to the cutting wires. This is accomplished by interconnecting the cutting wires 104 within the hub 103, as depicted in schematic of FIG. 9. The cutting wires 104 are shown connected in pairs by means of interconnected electrical conductors 212. Instead of using separate conductors, the wires may be joined for electrical contact in any suitable manner. Electrical current may be applied to the cutting wires 104 in shaft 110 by electrically conducting terminals 208 as generally depicted in FIG. 9. Cutting wires 104 are connected by means of electrical connector 213 to a switch unit 204 to which the appropriate current for such heating purposes is supplied from cable 206. The amount of electrical power and the frequency desired for the cutting operation is a matter of choice and will depend upon the requirements for the particular surgery procedure to be performed. The switch unit 204 may be any well-known switch configuration in which input current is supplied to one of conductor pairs 212. The return current path includes the other one of conductor pairs 212. Accordingly, in the configuration of this illustrative embodiment wherein two interconnected pairs of cutting wires are employed, one of the conductor pairs 212 will be input current conductors, and the other one of the conductor pairs will be return current conductors. Switch 204 is provided with a push button switch 205 which is operative to connect the input current of the desired magnitude and frequency from cable 206 to one of the conductor pairs 212 while the remaining conductor pair is connected to a return current lead of cable 206.

The cutting action of the cutting wires 104 may be further enhanced by vibratory motion. An ultrasonic transducer 203 in end cap transducer 101 is attached to the cutting wires 104 to impart ultrasonic vibration to the cutting wires. The vibrator may be any one of a number of well-known such devices and may be conveniently embedded within end cap transducer 101 of the shaft 110. Power for the transducer is provided by means of a pair of wires 209 connected to switch unit 204 and which may be interconnected with supply wires, likewise provided via cable 206 to switch 204, by operation of push button switch 207. The push button switch is preferably located near the distal end of the shaft 110 to conveniently allow the surgeon to selectively apply heat or vibratory motion to the cutting wires 104.

It will be understood that the above-described embodiments are only illustrative of the invention and that numerous other configurations may be devised by those skilled in the art without departing from the spirit and scope of the invention. It is contemplated that the ablation catheter may also be inserted in the fundus of a gallbladder via a retrograde route through the common and cystic ducts to ablate the mucosa of a gallbladder. The wires of the expandable basket would enlarge to engage the mucosal layer and apply radiofrequency current to heat and coagulate the mucosal layer. The ablation of the mucosal layer is known to prevent the reformation of gallbladder stones. Also contemplated is the use of the device for removing urinary obstructions in the urethra, especially in the prostatic urethra in men. Also it is contemplated that polyps in the intestinal tract can be removed with this device.

What is claimed is:

1. An ablation catheter comprising:
   an elongated member having a distal end;
   an expandable basket extending from said distal end of said member and having a plurality of helically-shaped wires, each of said wires having a circumferentially subscribing arc laterally overlapping at least one other of said wires for contacting and removing tissue from a surface of a body cavity or vessel, each arc of said wires having at least one corner formed therein for increasing the lateral orientation of the circumferentially subscribing arc with respect to said elongated member; and
   a hub interconnecting said plurality of wires at a distal end thereof.

2. The catheter of claim 1 wherein each of said hub and said elongated member includes a hollow passageway extending longitudinally therethrough and sized for insertion of a wire guide therethrough.

3. The catheter of claim 2 further comprising said wire guide sized for insertion through said hollow passageway of said hub and said elongated member.

4. The catheter of claim 1 wherein each of said basket wires comprises an electrical conductor.

5. The catheter of claim 1 further comprising a vibratory source positioned about said basket wires and in contact therewith to impart vibratory motion to said wires.

6. The catheter of claim 1 wherein said each of said wire arcs comprises a cutting instrument.

7. The catheter of claim 1 further comprising a telescoping adjustment rod connected to said hub and extending through a passageway of said member for controlling the expansion of , said basket.

8. The catheter of claim 7 further comprising a lock positioned about a proximal end of said member for fixedly positioning said telescoping adjustment rod in said member passageway.

9. The catheter of claim 1 further comprising an outer sheath having a hollow passageway extending longitudinally therethrough and sized for containment of said elongated member and said basket therein.

10. The catheter of claim 1 further comprising a net attached to said basket and extendable distally therefrom for collecting particulate therein.

11. An ablation catheter for removing obstructions from a constricted vessel or cavity, comprising:
  an outer sheath having a passageway positioned longitudinally therein and sized for insertion in a vessel;
  a moveable shaft having a cutting device attached to a distal end thereof, disposed in a telescoping relationship within said sheath passageway;
  said cutting device having at least one cutting edge and said shaft operable to extend said cutting device beyond a distal end of said sheath;
  said cutting device having one configuration when disposed within said sheath and another expanded configuration when extended beyond the distal end of said sheath, said at least one cutting edge having at least one corner for increasing the lateral orientation of the edge with respect to said movable shaft for contacting an interior surface of a vessel or cavity with said at least one cutting edge when extended beyond the distal end of said sheath;
  whereby obstructions may be separated from the interior surface of a vessel or cavity when said catheter is moved with said cutting device in said expanded configuration.

12. The catheter in accordance with claim 11 wherein said cutting device has an adjustable outer diameter in said expanded configuration and wherein said shaft is operable to selectively position said cutting device to a plurality of expanded positions having different outer diameters, to control said cutting device to cut said interior surface to different dimensions.

13. The catheter in accordance with claim 12 further comprising locking means for maintaining a selected outer diameter.

14. The catheter in accordance with claim 11 wherein said cutting device comprises a plurality of cutting wires.

15. The catheter in accordance with claim 14 wherein each of said cutting wires is preformed in a predetermined shape such that said plurality of wires presents a plurality of cutting edges forming an essentially cylindrical configuration in said expanded configuration, thereby presenting cutting edges substantially parallel to said interior surface for separating matter from said interior surface when said cutting device is extended beyond said distal end of said sheath.

16. The catheter in accordance with claim 14 wherein said wires comprise electrically conducting wires and said catheter further comprises electrical terminals connected to said wires for electrically heating said wires, whereby separation of matter from interior walls of a blood vessel is facilitated.

17. The catheter in accordance with claim 16 wherein each of said wires comprises a distal end and said plurality of wires comprises a first pair of wires joined at their distal ends to form a first conductive path for current applied to said terminals and a second pair or wires similarly joined at their distal ends to form a second conductive path for current applied to said terminals.

18. The catheter in accordance with claim 14 and further comprising a vibratory source attached to said cutting wires for imparting vibratory motion to said cutting wires, whereby separation of matter from said interior wall is facilitated.

19. The catheter in accordance with claim 18, wherein said wires comprise electrical conducting wires and said catheter further comprises electrical terminals connected to said wires for electrically heating said wires.

20. The catheter in accordance with claim 19 wherein each of said wires comprises a distal end and said plurality of wires comprises a first pair of wires joined at their distal ends to form a first conductive path for current applied to said terminals and a second pair of wires similarly joined at their distal ends to form a second conductive path for current applied to said terminals.

21. The catheter in accordance with claim 14 and further comprising a plurality of cords disposed between said cutting wires to form a net for collecting particulates separated from said surface by said cutting wires.

22. The catheter in accordance with claim 14 wherein each of said cutting wire comprises a distal end and said shaft is provided with a longitudinal passageway for accommodating a wire guide, said catheter further comprising a hub connected to said distal ends of said cutting wires and having a longitudinal passageway aligned with said passageway of said shaft for accommodating said wire guide.

23. The catheter in accordance with claim 22 and further comprising a collapsible net attached to said cutting wires for collecting particulates separated from said surface by said cutting device, having a distal end extending beyond said hub and a central opening aligned with said passageway of said hub for accommodating said wire guide.

24. The catheter in accordance with claim 11 and further comprising a net attached to said cutting device for collecting particulates separated from said surface by said cutting device.

25. An ablation catheter for removing obstructions from a constricted vessel or cavity, comprising:
  an outer sheath;
  a moveable shaft disposed in a telescoping relationship within said sheath and having a longitudinal passageway extending therethrough;
  a plurality of cutting wires attached to a distal end of said shaft, each of said cutting wires having a curved section forming a circumferentially subscribing arc for contacting and removing tissue from a surface of a body cavity or vessel, each arc of said wires having a corner formed therein for increasing the lateral orientation of the circumferentially subscribing arc with respect to said shaft, said curved section of each of said cutting wires disposed in an overlapping relationship with said curved section of at least one other of said cutting wires to form a circumferentially extending cutting area;
  a hub interconnecting distal ends of said cutting wires and having a longitudinally extending passageway for receiving a wire guide;
  an adjustment rod extending through said passageway of said shaft and connected to said hub and operable to move said hub relative to said distal end of said shaft to selectively expand and contract the diameter of said circumferentially extending cutting area, and having a longitudinally extending passageway for receiving a wire guide;

locking means attached to said shaft and operative to maintain said adjustment rod in a locked position in said shaft;

a plurality of electrical terminals connected to said cutting wires for heating said cutting wires;

a vibratory source in contact with said cutting wires to impart vibratory motion to said cutting wires; and a net disposed on a distal end of said catheter for collecting particulate therein.

* * * * *